US012465691B2

(12) United States Patent
Jaber

(10) Patent No.: US 12,465,691 B2
(45) Date of Patent: Nov. 11, 2025

(54) SYRINGE ASSEMBLY

(71) Applicant: JABER MEDICAL, PLLC, West University Place, TX (US)

(72) Inventor: Noor Mahmoud Jaber, West University Place, TX (US)

(73) Assignee: JABER MEDICAL, PLLC, West University Place, TX (US)

(*) Notice: Subject to any disclaimer, the term of this patent is extended or adjusted under 35 U.S.C. 154(b) by 1038 days.

(21) Appl. No.: 17/600,233

(22) PCT Filed: Mar. 27, 2020

(86) PCT No.: PCT/US2020/025248
§ 371 (c)(1),
(2) Date: Sep. 30, 2021

(87) PCT Pub. No.: WO2020/205531
PCT Pub. Date: Oct. 8, 2020

(65) Prior Publication Data

US 2022/0218909 A1 Jul. 14, 2022

Related U.S. Application Data

(60) Provisional application No. 62/827,156, filed on Mar. 31, 2019.

(51) Int. Cl.
*A61M 5/31* (2006.01)
*A61M 5/315* (2006.01)

(52) U.S. Cl.
CPC ...... *A61M 5/3134* (2013.01); *A61M 5/31511* (2013.01)

(58) Field of Classification Search
CPC ............ A61M 5/3134; A61M 5/31511; A61M 5/3286; A61M 2005/3118; A61M 2005/3201; A61M 5/3291
See application file for complete search history.

(56) References Cited

U.S. PATENT DOCUMENTS

| | | | | |
|---|---|---|---|---|
| 4,666,438 | A * | 5/1987 | Raulerson | A61M 5/158 604/272 |
| 5,026,354 | A * | 6/1991 | Kocses | A61M 5/50 604/110 |
| 6,530,903 | B2 * | 3/2003 | Wang | A61M 5/322 604/110 |
| 8,328,772 | B2 * | 12/2012 | Kinast | A61M 5/3286 604/274 |
| 2002/0133138 | A1 | 9/2002 | Pyret et al. | |
| 2010/0274190 | A1 | 10/2010 | Wayman et al. | |
| 2012/0226239 | A1 | 9/2012 | Green | |
| 2013/0079726 | A1 | 3/2013 | Madin | |
| 2013/0200549 | A1 * | 8/2013 | Felts | A61M 5/3134 264/275 |

* cited by examiner

*Primary Examiner* — Bradley J Osinski
(74) *Attorney, Agent, or Firm* — Womble Bond Dickinson (US) LLP

(57) ABSTRACT

Disclosed here are syringe assemblies that include a modified syringe tip to penetrate a subject to obtain or administer a substance. The syringe system consists of a syringe body with or without a modified syringe tip with a standard or modified plunger. The modified syringe tip or modified plunger protrusion can penetrate a subject, such as the skin of a patient or a membrane on sealing a container containing medicine, or a seal of an empty vial.

12 Claims, 11 Drawing Sheets

SYRINGE ASSEMBLY

CROSS REFERENCE TO RELATED APPLICATIONS

This application is a U.S. National Phase Under 35 U.S.C. § 371 of International Application No. PCT/US2020/025248, titled "SYRINGE ASSEMBLY," filed Mar. 27, 2020, which is a PCT application claiming priority to and the benefit of U.S. Provisional Application No. 62/827,156, titled "INTEGRATED NEEDLE-SYRINGE SYSTEM," filed Mar. 31, 2019, which is incorporated herein in its entirety by reference.

TECHNICAL FIELD

This disclosure generally relates to syringes, including disposable syringes, pre-filled syringes, and syringes in which the injection substance is not pre-filled. This disclosure also includes an apparatus to aspirate a substance from a container, such as an IV bag or a medicine vial with a flexible membrane, into the syringe without the need for any additional components.

BACKGROUND

Billions of injections are made annually. Many medicines are supplied in vials sealed with a flexible membrane that is pierced in order to fill the syringe for injection. Injections typically involve using a disposable syringe and a blunt needle, made of metal or plastic, to draw up medicine from a container and then deliver the medicine using the syringe with a different needle. Medicines are provided in different physical forms, including as powders, solids such as microcapsules, granules and tablets, or liquid. The needles used to draw up the medicine can be sharp but are typically full-length, blunt metal needles or shorter plastic needles. Needle-stick injuries continue to occur with blunt needles.

SUMMARY

Embodiments disclosed here are designed to decrease needle-stick injuries while eliminating additional components for drawing up medicines from containers. Certain embodiments also result in reduction of material consumption, thus leading to a decrease in costs and environmental impact. Embodiments of the syringe system described here can be used with any container. The containers can be filled or devoid of a substance and the syringe system can be used to draw the substance from the container or expel substance into the containers. This syringe system can be used with containers with or without a membrane, potentially enclosing a substance inside.

Disclosed here are embodiments of the syringe system and methods of using the syringe systems in various applications. In an embodiment, the syringe system has the following components: a barrel with a tip and a plunger. The barrel of the syringe system encloses a chamber, which is the volume into which substances can be drawn into during use. The barrel and the chamber can take any shape. In an embodiment, the barrel and the chamber are cylindrical. In an embodiment, the chamber is cylindrical but the barrel is modified to provide protrusions for finger placement. One end of the barrel is adapted to receive a needle and this end is referred to as the tip. The other end of the barrel is adapted to receive a plunger. The plunger has a flange at one and a seal at the other end. The plunger slides within the chamber, and is operated to draw up or expel substance(s) from the chamber through the outlet in the tip of the barrel. The plunger can be modified for specific use cases. In an embodiment, the flange of the plunger has a circular protrusion for thumb placement. The tip of the syringe, through which a substance is drawn or expelled through an opening, can protrude singularly from the body of the syringe. In an embodiment, the tip can incorporate a locking system, such as a Luer lock. The tip can be flat or shaped to match a specific plunger shape. Where this syringe system differs from current syringes is the tip of the distal portion. The tip is designed such that, if necessary, it can penetrate membranes containing substances, such as medicines and intravenous fluid. The tip can take a variety of shapes to accomplish this. The tip can be made of any material compatible for the applications disclosed here. In certain embodiments, the tip is made of plastic. In certain embodiments, the tip is made of metal alloys, such as stainless steel. This syringe system requires no additional components to penetrate the containers. The tip is configured to accommodate a needle, such as one for injection of a medication, and create a seal if needed. In an embodiment, the tip of the syringe system is adapted with an integrated lock, such as a Luer lock, to secure a needle about the tip of the syringe. In an embodiment, the tip has two or more vents to facilitate aspiration and expulsion of substances. In certain embodiments, the tip is adapted to prevent it from sliding out of a membrane on a container or from the container itself by the use of a slot or a circumferential indentation on the tip that engages with the membrane and prevents slippage. In another embodiment, the tip is fitted with a filter. This filter can be housed within the tip of the syringe system. The filter prevents certain particles from entering the interior chamber of the syringe. In another application, the filter prevents certain particles from leaving the chamber. These particles would be those not intended to be administered or expelled from the syringe.

In another embodiment, a syringe system contains a barrel and a plunger adapted with a protrusion. This protrusion can extend past an outlet of the tip of a syringe and permits penetration of a membrane of a container or the container itself to facilitate the aspiration of a substances, such as medicines into the chamber of the syringe. The protrusion can include a locking mechanism. The protrusion can take a variety of shapes. The protrusion can be made of any material compatible for the applications disclosed here. In certain embodiments, the protrusion is made of plastic. In certain embodiments, the protrusion is made of a metal alloy, such as stainless steel. When the plunger is engaged fully within the chamber, the protrusion extends beyond the outlet of the tip. Once the protrusion pierces through a membrane of a container or the container itself, it allows engagement of the tip with the membrane of a container or the container itself. Then, by sliding the plunger away from the tip of the barrel, substances from the container can be aspirated into the chamber. In an embodiment, the tip of the syringe is tapered to facilitate easy entry into the container. The tip of the syringe can also be modified to prevent slippage from the membrane of a container or the container itself by a slot or a circumferential indentation. The protrusion of the plunger may be solid or may have an interior lumen with or without accompanying vent. While the protrusion will extend past the outlet of the syringe, it will not impede upon the ability of the tip to engage devices typically connected to a syringe, such as standard or safety injection needles, IV ports and caps, among others. The protrusion can be housed within the hub of a needle and an adequate seal can be made. The plunger in this system can be modified such that the flange of the plunger has a circular protrusion for thumb placement. The shaft of the plunger can have reinforcement ridges. The plunger can incorporate a membrane, usually plastic or rubber, to go about the protrusion and onto the portion of the plunger that slides into the syringe chamber such that it can create a seal to keep substances within the syringe chamber.

In one aspect, the disclosure is generally directed to a syringe assembly. The syringe assembly comprising a barrel having an open proximal end, a distal end, and a chamber. A plunger is slidingly received in the chamber for drawing fluid into the chamber and discharging fluid from the chamber. The barrel has a tip at the distal end. The tip having a lumen extending through the length of the tip. The tip has a beveled end for penetrating a membrane and allowing fluid communication between the chamber and the fluid contained by the membrane.

In another aspect, the disclosure is generally directed to a syringe assembly. The syringe assembly comprising a barrel having an open proximal end, a distal end, and a chamber. A plunger is slidingly received in the chamber for drawing fluid into the chamber and discharging fluid from the chamber. The barrel has a tip at the distal end. The tip having a lumen extending through the length of the tip. The tip is generally hollow cylindrically shaped with a blunt end. The plunger has a protrusion for extending through the lumen and penetrating a membrane and allowing fluid communication between the chamber and the fluid contained by the membrane.

BRIEF DESCRIPTION OF THE DRAWINGS

The present disclosure can be better understood by referring to the following figures. The components in the figures are not necessarily to scale. The emphasis is instead placed upon illustrating the principles of the disclosure.

DETAILED DESCRIPTION

Figure 1:
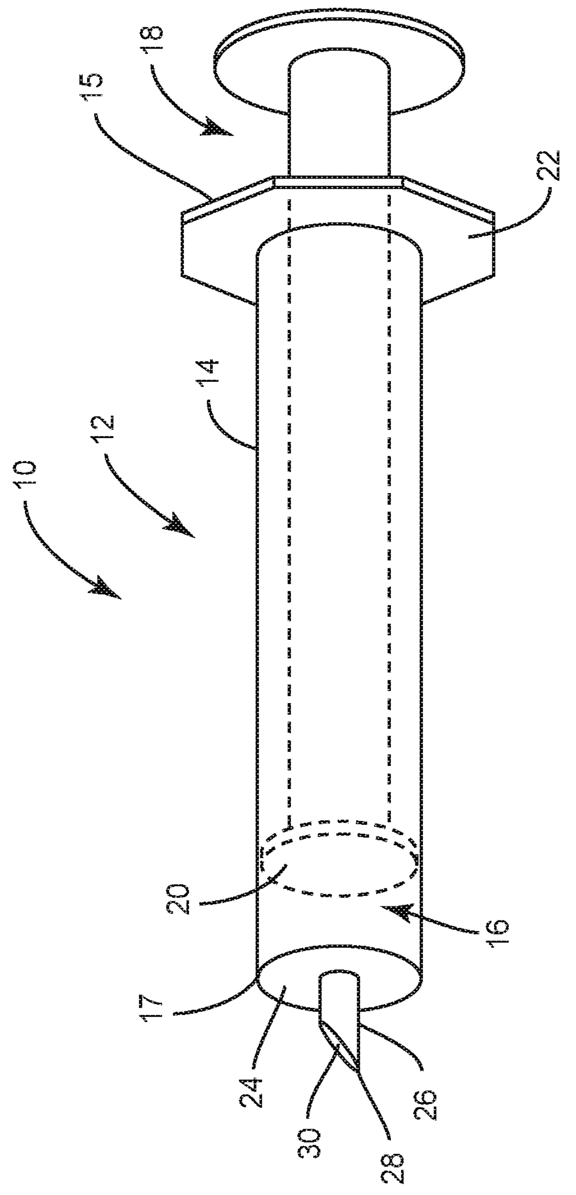
FIG. 1 is an assembled perspective view of a syringe assembly, according to an embodiment of the disclosure.

FIGS. 1-5B show one embodiment of a syringe assembly 10, which is used for injecting or drawing a substance or a fluid from a subject S. In various embodiments of the disclosure, the subject S can include a patient of specimen, such as the tissue of an animal or human, as well as inanimate objects such as containers or other devices for holding a fluid. The syringe assembly 10 includes a syringe 12 that includes a barrel 14 which is substantially cylindrical. The barrel 14 has an open proximal end 15, a distal end 17, and a chamber 16 defined therein. A fluid 19 housed in the chamber 16 is injected into or drawn from the subject S. The syringe assembly 10 further includes a plunger 18. The plunger 18 is an elongated cylindrical member that is slidingly received within the chamber 16. The plunger 18 is configured to fit within the chamber 16 in a frictional fit and to reciprocate within the chamber 16 and further includes a plunger head 20. In embodiments, the plunger may include reinforcement ribs (not shown). Drawing fluid 19 into the chamber 16 or discharging fluid 19 from the chamber 16 are accomplished by respectively reciprocating the plunger head 20 toward the open proximal end 15 of the chamber 16 or reciprocating the plunger head 20 toward the distal end 17 of the chamber 16. The barrel 14 further has a finger guard or planar flange 22 extending laterally from the proximal end 15 of the barrel 14. The finger guard 22 is configured to assist in reciprocating the plunger 18 toward or away from the proximal end 15 of the barrel 14.

Referring further to FIGS. 1-5B, the barrel 14 has a tip or cannula 26 extending from an external end surface 24 at the distal end 17 of the barrel 14. In one embodiment, the tip 26 is generally cylindrically shaped with a lumen or passage 30 extending the length of the tip 26. The passage 30 of the tip 26 is configured to allow fluid communication from and to the chamber 16. In certain embodiments, the tip 26 further has a beveled end or point 28 that defines a sharp end suitable for penetrating a membrane 50 of the subject S and to allow fluid communication between the chamber 16 and the subject. In other embodiments, the tip 26 and/or the point 28 could be alternatively shaped, arranged, configured and/or omitted without departing from the disclosure. Further, the subject S can have the membrane 50 or the subject can be a material without a membrane (e.g., the tissue of a patient) and the point 28 of the tip 26 can facilitate penetration of the surface of the subject not having a membrane without departing from the scope of the disclosure.

Figure 4A:
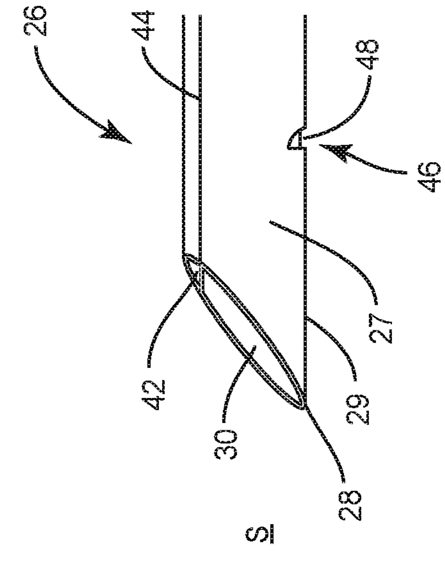
FIG. 4A and FIG. 4B are close-up side views of syringe tips for stabilization in a barrier and past the barrier respectively, according to an embodiment of the disclosure.
Figure 4B:
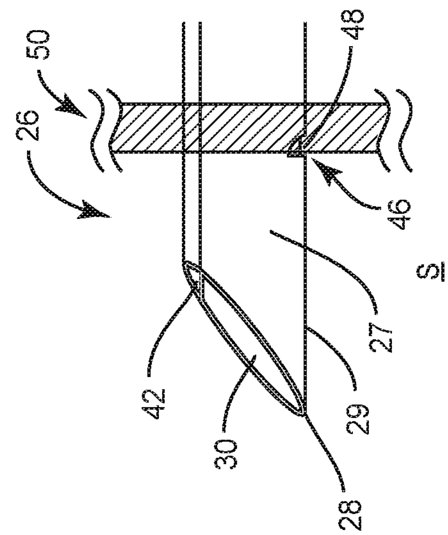

In certain embodiments, as illustrated in FIGS. 1, 4A-4B, and 5A-5B, the tip 26 provides direct or needleless access to the subject S to allow fluid communication from and to the chamber 16. In such a configuration, the tip 26 is configured to provide access to a variety of medicine delivery access points. In an embodiment illustrated in FIGS. 4A and 4B, the tip 26 has a generally cylindrical body 27 that has at least one indentation 46 in an external surface 29 of the body 27 for engaging the membrane 50 of the subject S. The indentation 46 allows for stabilization of the tip 26 in the membrane 50 of the subject S. For instance, the membrane 50 includes a material that serves as a barrier, including, but not limited to a tissue of an animal or a membrane of a container. The indentation 46 includes a notch or recess 48 in a portion of the external surface 29 of the body 27. In the illustrated embodiment, the notch 48 has edges in the external surface 29 of the body 27 and is shaped to extend less than circumferentially around the external surface 29. As indicated in FIG. 4B, the tip 26 with the indentation 46 engages the membrane 50 via the notch 48 after penetration and advancement of the tip 26 past the membrane 50 and into the subject S. While a single indentation 46 is illustrated in FIGS. 4A-4B, the tip 26 could be alternatively configured with multiple indentations or the indentation could be shaped, arranged, or configured otherwise without departing from the disclosure. For instance, in embodiments, the tip 26 includes a partially or circumferentially protruding rib (not shown) that engages the membrane 50 of the subject S. The tip 26 illustrated in FIGS. 4A-4B further includes a vent 42 including a passage or lumen 44 formed axially within a portion of the tip 26 that allows for air or other supplemental fluids to communicate with the chamber 16. In some embodiments, the vent 42 can be used to allow fluid under pressure (i.e., fluid contained in venous/arterial vessels, other positive pressure fluid transfers, etc.) to flow into or out of the chamber 16.

Figure 5B:
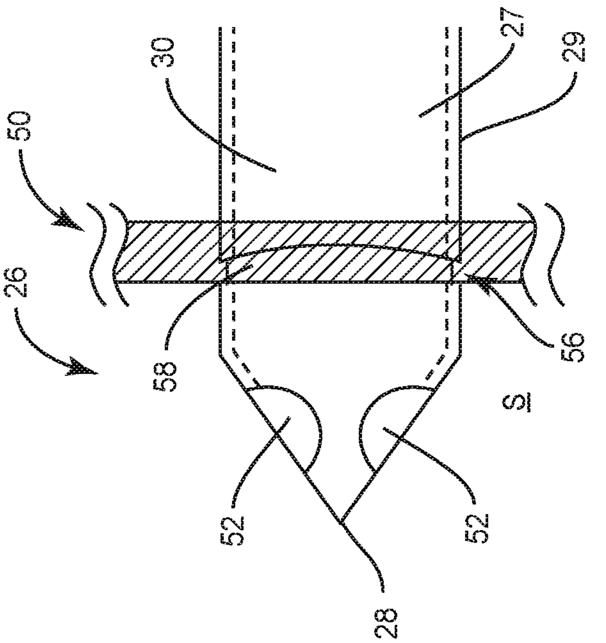
FIG. 5A and FIG. 5B are close-up side views of additional syringe tips for stabilization in a barrier and past the barrier respectively, according to an embodiment of the disclosure.
Figure 5A:
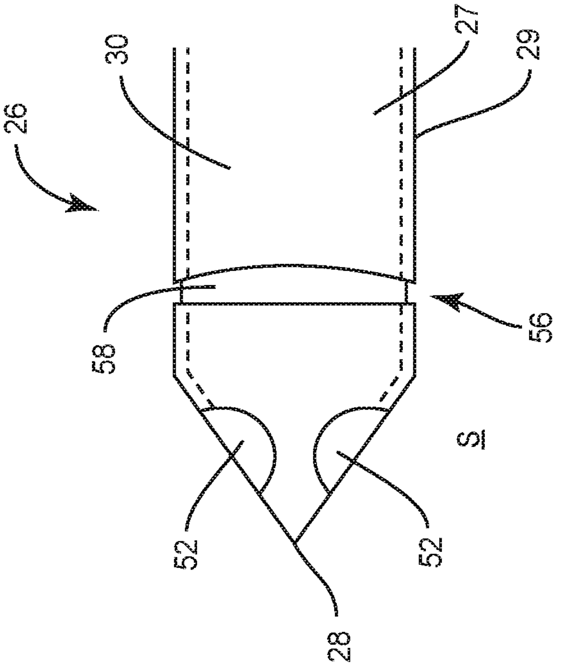
Figure 6:
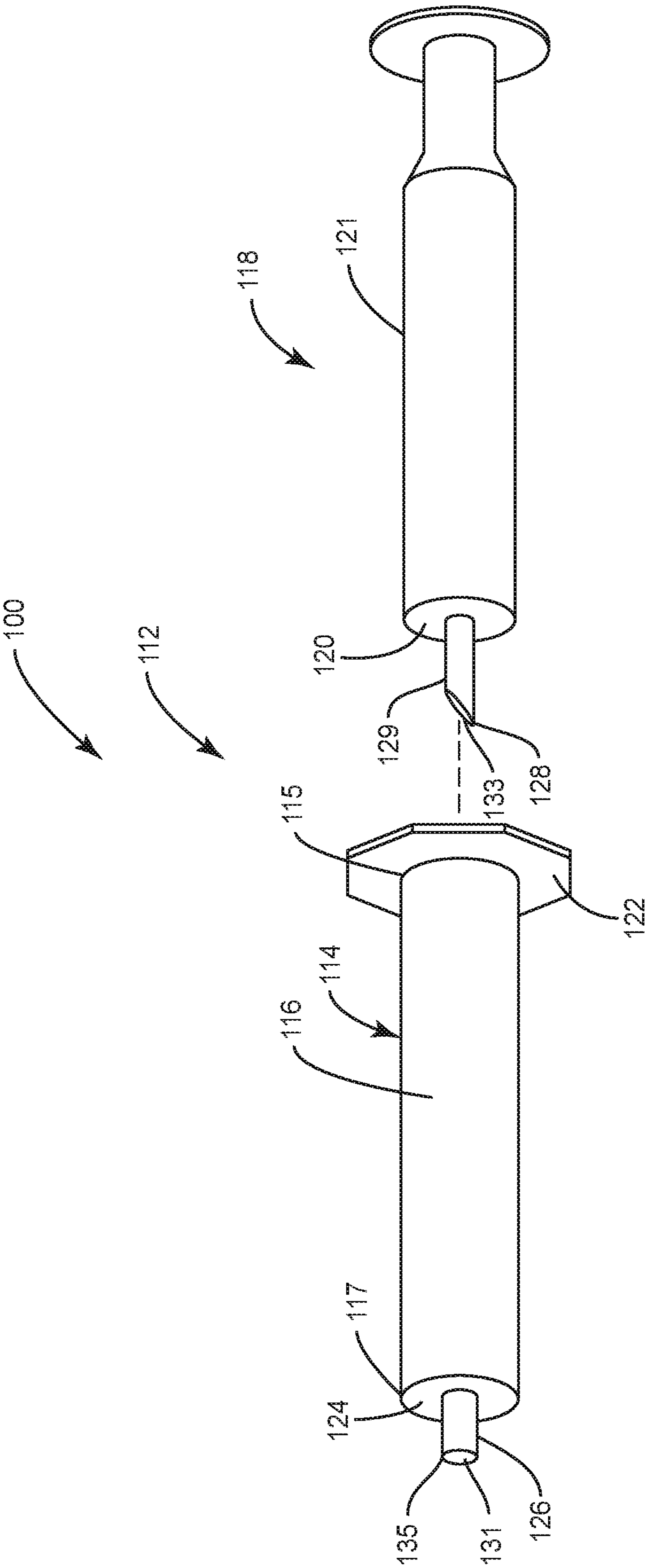
FIG. 6 is a disassembled perspective view of a syringe assembly, according to a second embodiment of the disclosure.

In another embodiment illustrated in FIGS. 5A-5B, an indentation 56 is a notch 58 in a portion of the external surface 29 of the body 27 of the tip 26 that is shaped to extend circumferentially around the external surface 29. In this embodiment, the tip 26 is cylindrically shaped with a central point 28 that defines a sharp end suitable for penetrating through the membrane 50 of the subject S. The indentation 56 allows for stabilization of the tip 26 in the membrane 50 of the subject S. As indicated in FIG. 5B, the tip 26 with the indentation 56 engages the membrane 50 via the notch 58 after penetration and advancement of the tip 26 past the membrane 50 and into the subject S. The tip 26 illustrated in FIGS. 5A-5B further includes passages or fenestrations 52 that are in fluid communication with the lumen or passage 30. The passages 52 allow fluid to communication between the chamber 16 and the subject S. In some embodiments, the passages 52 can extend axially within a portion of the tip 26 creating a pathway for air and other fluids to allow supplemental fluid communication with the chamber 16.

Figure 2:
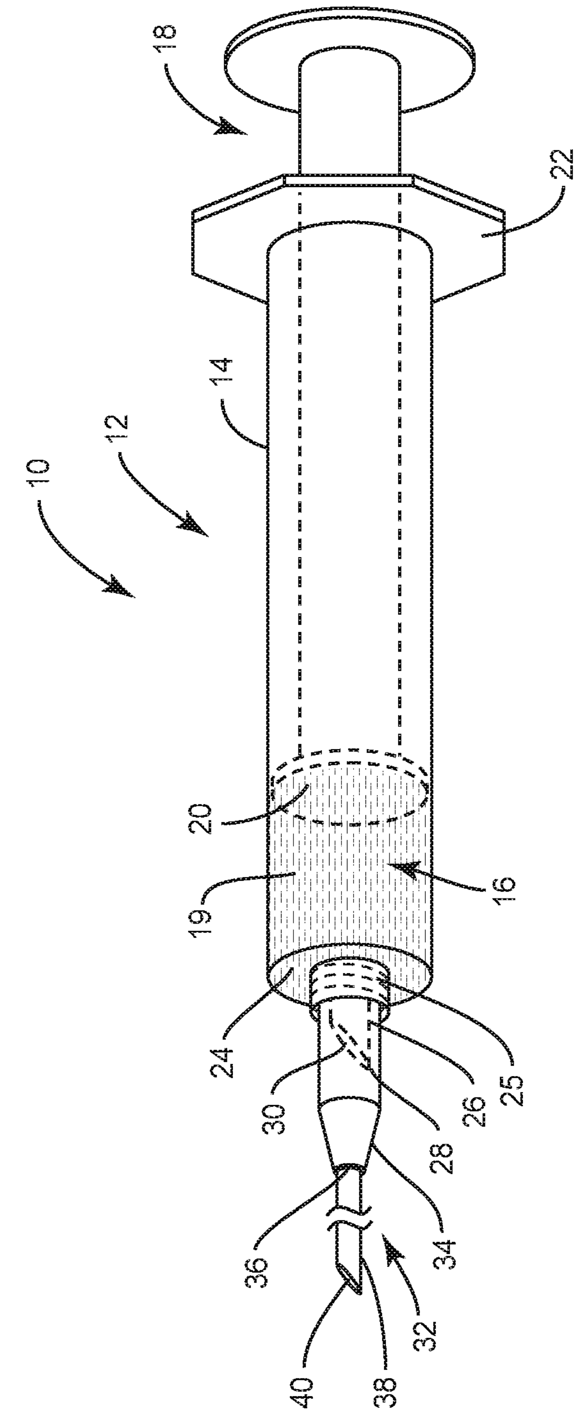
FIG. 2 is an assembled perspective view of the syringe assembly with a Luer-lock collar engaged with a needle assembly, according to an embodiment of the disclosure.
Figure 3:
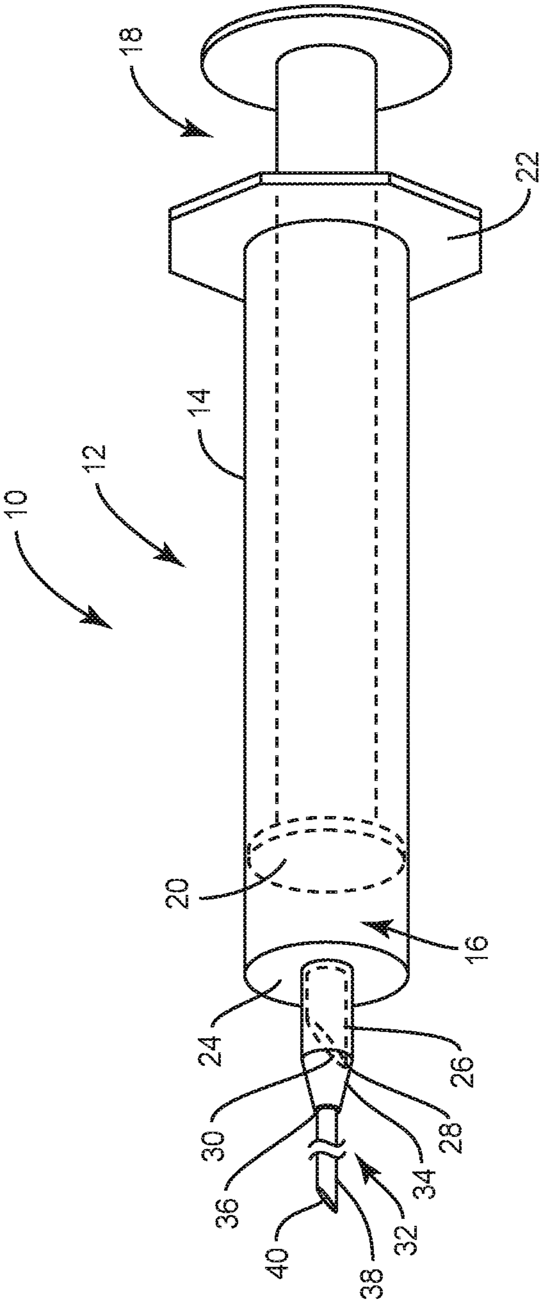
FIG. 3 is an assembled perspective view of a syringe assembly with a Luer-slip type engagement with a needle assembly, according to an embodiment of the disclosure.

Apart from providing needleless access to a variety of medicine access systems, the syringe system 10 is also configured to receive one or more needle assembly systems for hypodermic injections and other such procedures. For example, referring to FIGS. 2-3, the syringe assembly 10 cooperates with a releasably attached needle assembly 32. In an embodiment illustrated in FIG. 2, the barrel 14 of the syringe assembly 10 includes a collar 25 extending from the external end surface 24. The collar 25 is generally concentric with the tip 26 of the syringe assembly 10 and is configured to attach the barrel 14 to the needle assembly 32. The needle assembly 32 includes a frustoconical shaped hub 34, an axial passageway 30 extending axially through the needle shaft 38, and a beveled end 40 on the free end of the needle shaft 38 that defines a sharp end suitable for penetrating through the outer surface or membrane 50 of the subject S. As illustrated in FIG. 2, the collar 25 can generally be of a hollow cylindrical shape with internal threads configured to attach the needle assembly 32 via a Luer-lock mechanism. In another embodiment illustrated in FIG. 3, the collar 25 can be dispensed with and the needle assembly 32 can be attached in a tight frictional fit directly with the tip 26 via a Luer-slip mechanism. In such a configuration, the tip 26 may have a tapered external surface to receive and hold the needle assembly 32 in a tight frictional fit. The syringe system 10 could include other attachment features for attachment to a needle assemble or for connection to other suitable delivery devices and/or storage mediums (e.g., connectors, intravenous bags or fluid storage, intravenous pumps or pump connectors, etc.) and the attachment features shown and described could be otherwise shaped, arranged, configured, and/or omitted without departing from the scope of the disclosure.

FIGS. 6-11C show a second embodiment of a syringe assembly 100 used for injecting or drawing a substance or a fluid from the subject S. As described earlier, the subject S can include a patient, such as an animal or human, as well as inanimate objects such as containers. The syringe assembly 100 includes a syringe 112 that includes a barrel 114 which is generally substantially cylindrical. The barrel 114 has an open proximal end 115, a distal end 117, and a chamber 116 defined therein. A fluid housed in the chamber 116 is injected into or drawn from the subject S. The syringe assembly 100 further includes a plunger 118. The plunger 118 is an elongated cylindrical member with a body 121 and a plunger head 120 that is slidingly received within the chamber 116 for drawing fluid into the chamber and discharging fluid from the chamber. Once the body 121 of the plunger 118 is inserted into the chamber 116 of the barrel 114, the plunger 118 is configured to reciprocate within the chamber 116 and draw fluid into the chamber 116 or discharge fluid from the chamber 116. This is accomplished by reciprocating the plunger head 120 toward the open proximal end 115 of the chamber 116 or reciprocating the plunger head 120 toward the distal end 117 of the chamber 116 respectively. The barrel 114 further has a finger guard or planar flange 122 extending laterally from the proximal end 115 of the barrel 114. The finger guard 122 is configured to assist in reciprocating the plunger 118 toward or away from the proximal end 115 of the barrel 114.

Referring further to FIGS. 6-11C, the barrel 114 has a tip or cannula 126 extending from an external end surface 124 at the distal end 117 of the barrel 114. The tip 126 is generally cylindrically shaped with a lumen or passage 131 extending the length of the tip 126. The passage 131 of the tip 126 is configured to allow fluid communication to the chamber 116. For example, when the plunger 118 of the syringe assembly 100 is reciprocated towards the proximal end 115 of the barrel 116, fluid from a membrane is drawn into the chamber via the passage 131 of the tip 126. In certain embodiments, the tip 26 is generally hollow cylindrically shaped with a blunt end 135.

The plunger 118 further has a protrusion 129 that is configured to extend through and past the passage 131 and penetrate a membrane to allow fluid communication between the chamber 116 and the fluid contained by the membrane when the plunger 118 is received within the barrel 114. In the illustrated embodiment, the protrusion 129 is generally cylindrically shaped, solid body that extends from the plunger head 120 with a beveled end 128. In alternative embodiments, the protrusion 129 could be configured to include a lumen or passage to allow fluid communication through the protrusion. In the illustrated embodiment, the protrusion 129 includes a pointed end 133 suitable for penetrating a membrane 150 of the subject S. In other embodiments, the protrusion 129, the beveled end 128 and/or the pointed end 133 could be alternatively shaped, arranged, configured and/or omitted without departing from the disclosure.

In certain embodiments, as illustrated in FIGS. 6, 7A, 9A-9C, 10A-10C, and 11A-11C, the syringe assembly 100 provides direct or needleless access to the subject S to allow fluid communication from and to the chamber 16. In such configurations, both the tip 126 of the barrel 114 and the protrusion 129 of the plunger 118 may configured to draw fluid into the syringe assembly when the plunger 118 is reciprocated toward the proximal end 115 of the barrel 114. During injection or expulsion of fluid from the syringe assembly 100, fluid is initially expelled through the tip 126 of the barrel 114 when the plunger 118 is reciprocated toward the distal end 117 of the barrel. Once the protrusion 129 extends past the tip 131, the pointed end 133 of the plunger 118 can engage the membrane 150 of the subject S to allow fluid transfer between the chamber 114 and the subject. In such a needleless configuration, the protrusion 129 is configured to provide access to a variety of medicine delivery access points.

Figure 7A:
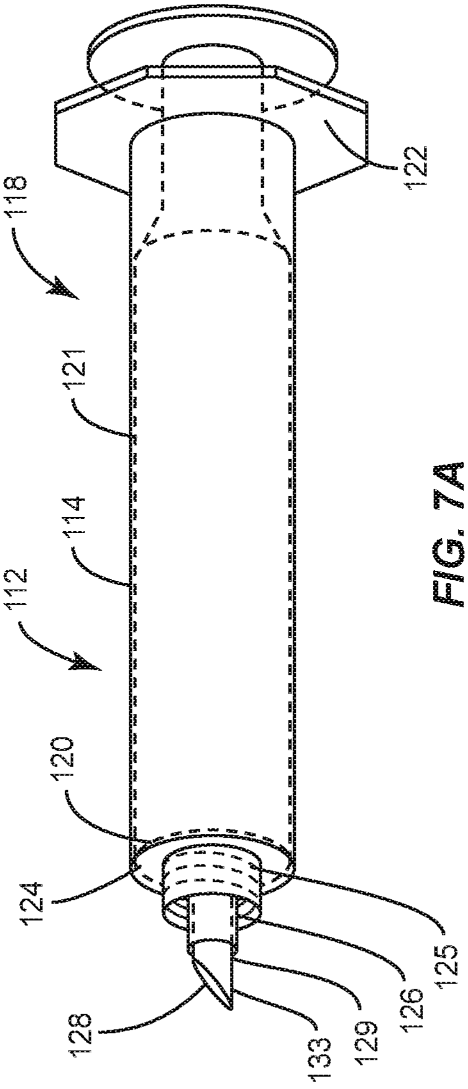
FIG. 7A and FIG. 7B are assembled perspective views of the syringe assembly of the second embodiment with a Luer-lock collar and with the Luer-lock collar engaged with a needle assembly respectively.
Figure 7B:
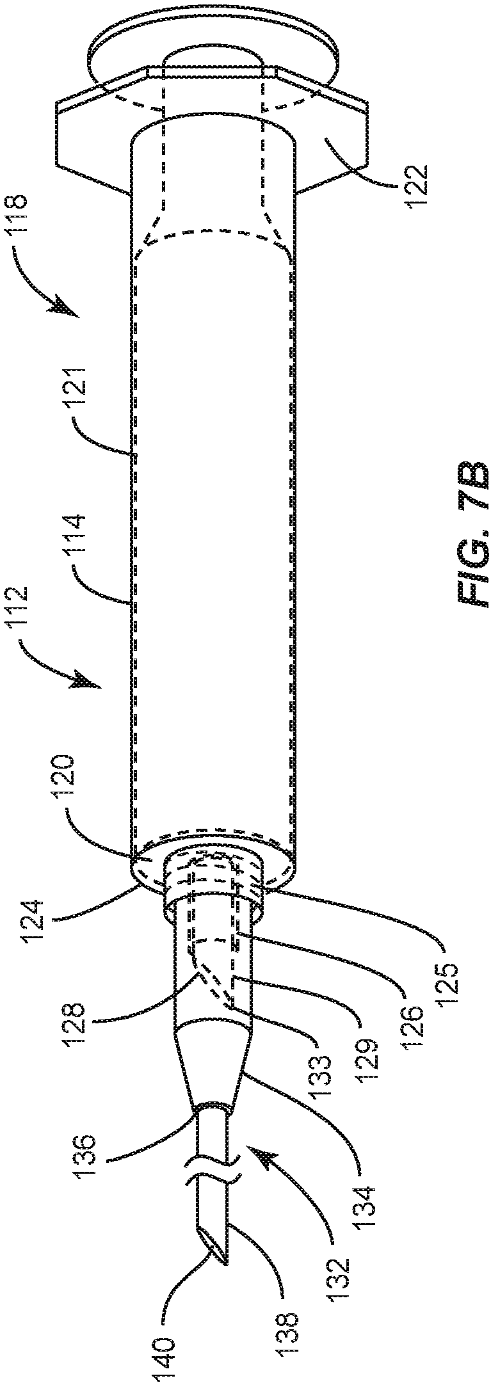
Figure 8:
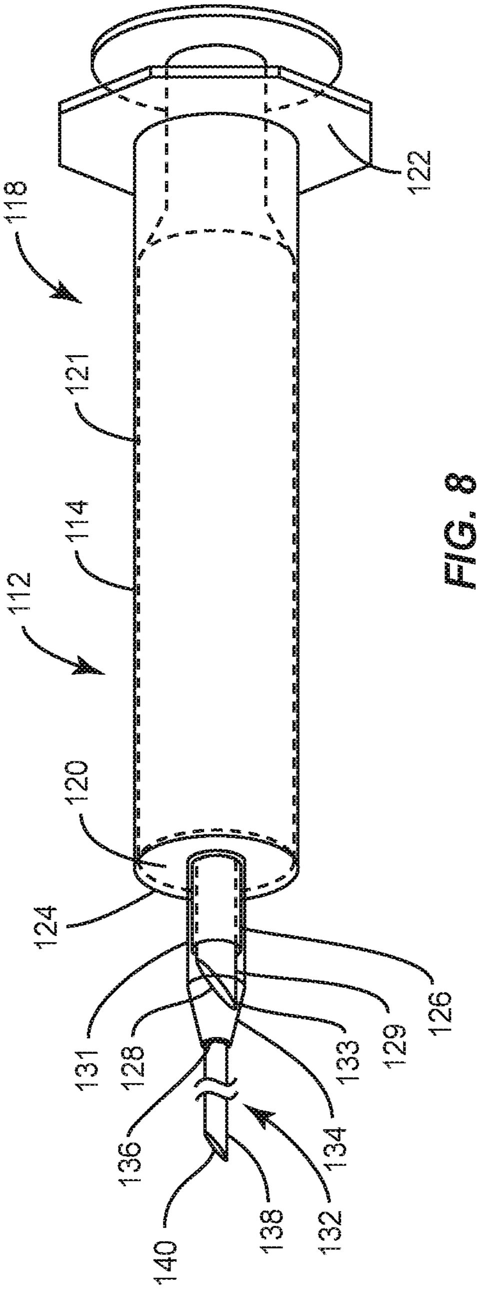
FIG. 8 is an assembled perspective view of the syringe assembly of the second embodiment with a Luer-slip type engagement with a needle assembly.

Apart from providing needleless access to a variety of medicine access systems, the syringe system 100 is also configured to receive one or more needle assembly systems for hypodermic injections and other such procedures. For example, referring to embodiments illustrated in FIGS. 7A-7B and 8, the syringe assembly 100 is configured to cooperate with a releasably attached needle assembly 132. The needle assembly 132 includes a frustoconical shaped hub 134, an axial passageway 136 extending axially through the needle shaft 138, and a beveled end 140 on the free end of the needle shaft 138 that defines a sharp end suitable for penetrating through the outer surface of a subject. As illustrated in FIGS. 7A-7B, the barrel 114 of the syringe assembly 100 includes a collar 125 extending from the external end surface 124. The collar 125 is generally concentric with the tip 126 of the barrel 114 and is configured to attach the barrel 114 to the needle assembly 132. As illustrated in FIGS. 7A-7B, the collar 125 can generally be of a hollow cylindrical shape with internal threads configured to be attached to the needle assembly 132 via a Luer-lock mechanism. As with the first embodiment, the collar 125 can also be configured to receive other external medicine needle hubs or attachment devices that use the Luer-lock mechanism. In another embodiment illustrated in FIG. 8, the needle assembly 132 can be attached to the syringe assembly 100 in a tight frictional fit with the tip 126 via a Luer-slip mechanism. In such a case, the tip 126 can have a tapered external surface that is configured for a Luer-slip connection. The syringe assembly 100 could include other attachment features for attachment to a needle assemble or for connection to other suitable delivery devices and/or storage mediums (e.g., connectors, intravenous bags or fluid storage, intravenous pumps or pump connectors, etc.) and the attachment features shown and described could be otherwise shaped, arranged, configured, and/or omitted without departing from the scope of the disclosure.

Figures 9A, 9B, 9C:
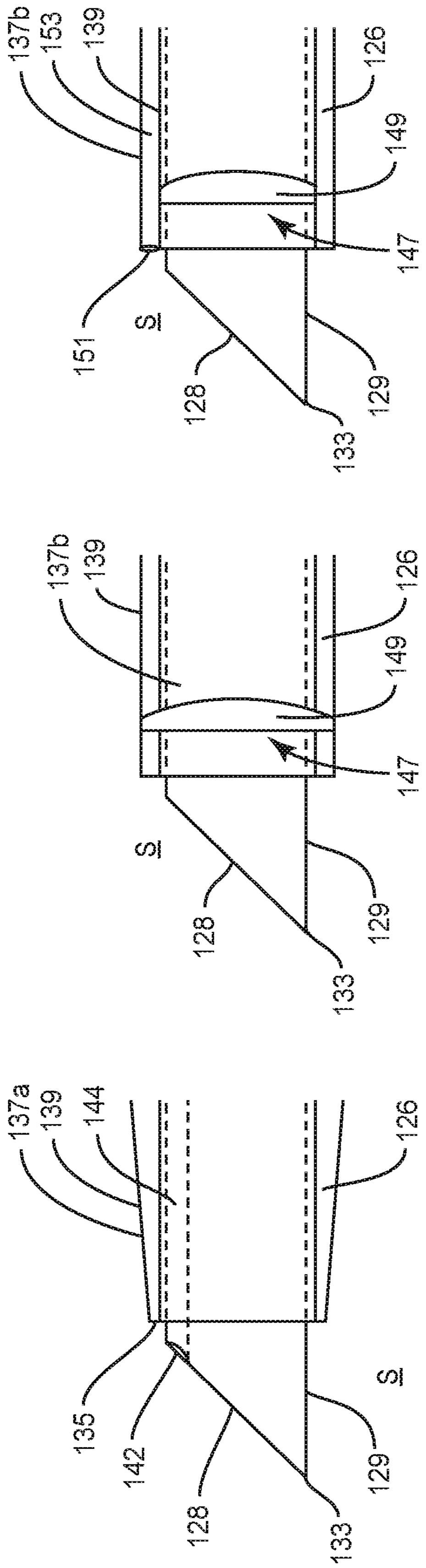
FIGS. 9A, 9B and 9C are close-up side views of syringe tips and plunger protrusions, according to an embodiment of the disclosure.

Referring now to FIGS. 9A-9C and 10A-10B, close-up side views of the syringe assembly 100 with the plunger protrusion 129 received in the tip 126. The plunger protrusion 129 is shown to be fully engaged inside and extending past the tip 126 of the barrel 114. In the embodiment illustrated in FIG. 9A, the tip 126 of the barrel 114 is a tapered or frustoconical shaped configuration and has a generally frustoconical shaped body 137*a*, while in the embodiments illustrated in FIGS. 9B and 9C, the tip 126 has a generally cylindrical shaped configuration and a generally cylindrical shaped body 137*b*. As shown in FIGS. 9B and 9C, the generally cylindrical body 137*b* has at least one indentation 147 in an external surface 139 of the body 137 for engaging the membrane 150 of the subject S. The indentation 147 allows for stabilization of the tip 126 and protrusion 129 in the membrane 150 of the subject S. For instance, the membrane 150 includes a material that serves as a barrier, including, but not limited to a tissue of an animal or a membrane of a container. In one embodiment, the indentation 147 is a notch or recess 149 in a portion of the external surface 139 of the body 137*b*. As indicated in FIG. 9C, the notch 149 has edges in the external surface 139 of the body 137*b* and is shaped to extend less than circumferentially around the external surface 139. Alternatively, as illustrated in FIGS. 9B and 10A-10C, the notch 149 may be shaped to extend circumferentially around the external surface 139 of the body 137*b*.

Figure 10C:
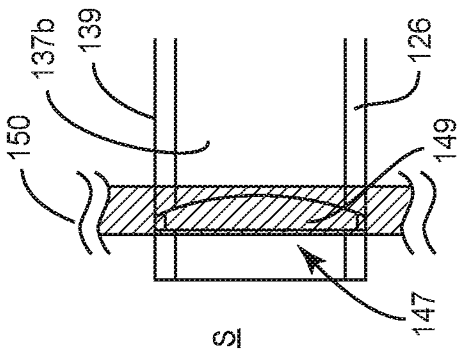
FIGS. 10A, 10B and 10C are close-up side views of syringe tips with a circumferential indentation, according to an embodiment of the disclosure.
Figure 10B:
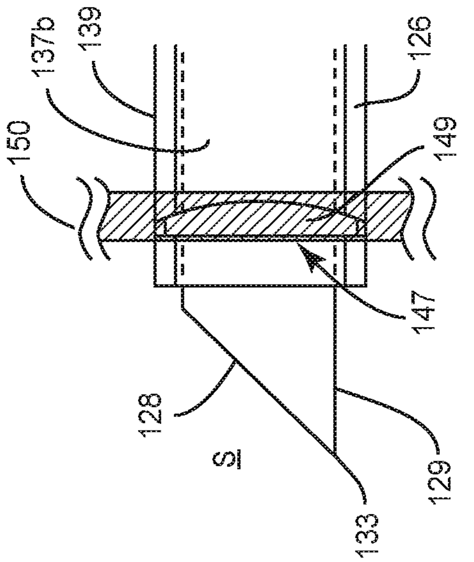
Figure 10A:
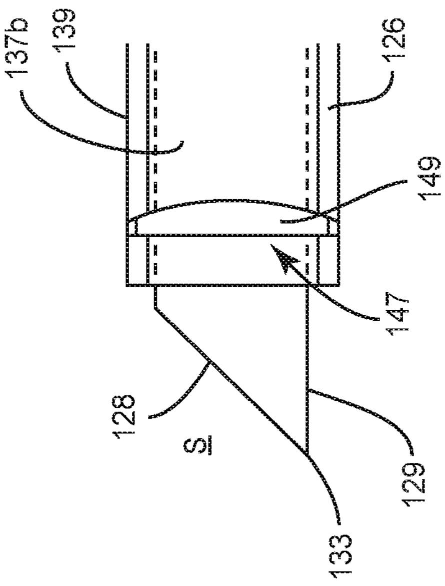

As further indicated in FIG. 10B, the tip 126 has been first used to penetrate the membrane 150 and the syringe assembly further inserted through the member so that the indentation 147 of the body 137*a* of the tip 126 engages the membrane 150 via the notch 149 after penetration and advancement of the tip 126 and protrusion 129 past the membrane 150 and into the subject S. As shown in FIG. 10C, the plunger may be withdrawn in the chamber 114 so that the protrusion 129 is removed from the tip 126 after the tip 126 of the barrel 114 engages the membrane 150. While a single indentation 147 is illustrated in FIGS. 9B-9C and 10A-10C, the tip 126 could be alternatively configured with multiple indentations or the indentation 147 could be shaped, arranged, or configured otherwise without departing from the disclosure. For instance, in other embodiments, the tip 126 includes a partially or circumferentially protruding rib that engages the membrane 150 of the subject S. In the embodiment of FIG. 9A, the protrusion 129 includes a vent 142 including a passage or lumen 144 formed axially and adjacent the beveled end 128 of the protrusion 129 that allows for air or other supplemental fluids to communicate with the chamber 116. In another embodiment illustrated in FIG. 9C, the tip 126 of the barrel 114 further includes a vent 151 including a passage or lumen 153 formed axially within a portion of the tip 126 that allows for air or other supplemental fluids to communicate with the chamber 116. In some embodiments, the vents 142, 151 can be used to allow fluid under pressure (i.e., fluid contained in venous/arterial vessels, or other positive pressure fluid transfers, etc.) to flow into or out of the chamber 116.

Figure 11C:
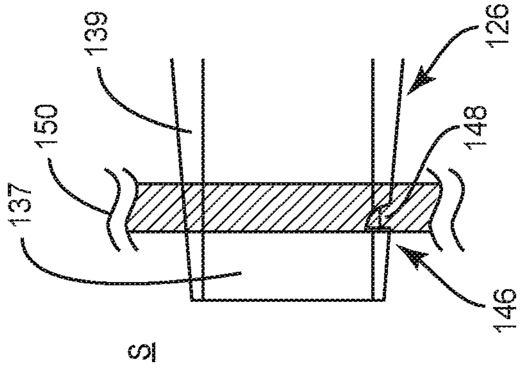
FIGS. 11A, 11B and 11C are close-up side views of a tapered syringe tip with a notch, according to an embodiment of the disclosure.
Figure 11B:
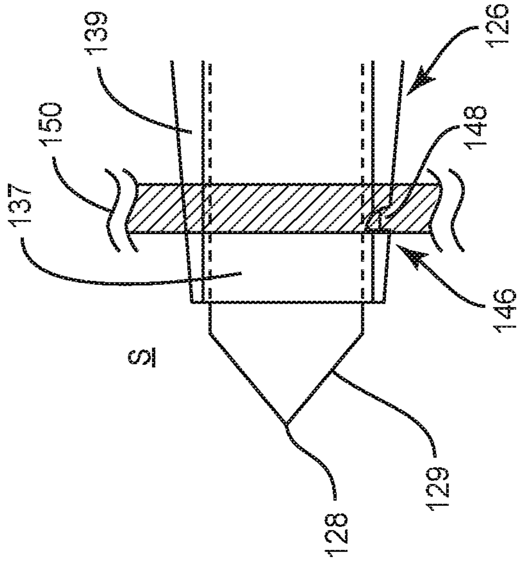
Figure 11A:
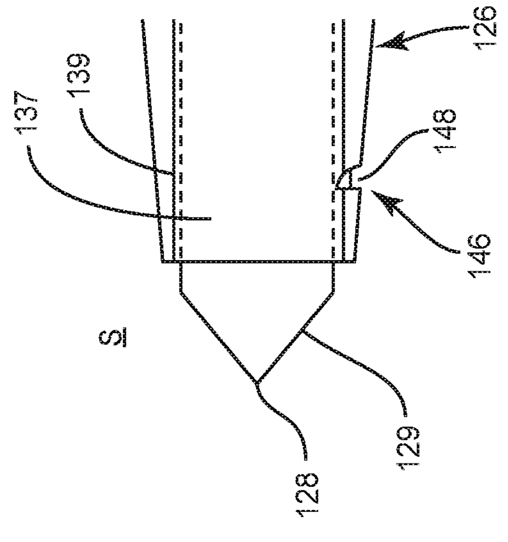

In another embodiment illustrated in FIGS. 11A-11C, an indentation 146 is a notch 148 in a portion of the external surface 139 of the body 137 of the tip 126 that is shaped to extend less than circumferentially around the external surface 139. In this embodiment, the plunger protrusion 129 is generally cylindrically shaped with a central point 128 that defines a sharp end suitable for penetrating through a membrane 150 of the subject. In the embodiment of FIG. 11A, the tip 126 of the barrel 114 is generally tapered with a frustoconical shaped body. The indentation 146 allows for stabilization of the tip 126 in the membrane 150 of the subject S. As indicated in FIG. 11B, the tip 126 with the indentation and the protrusion 129 can be pressed through the membrane 150 with the notch 148 engaging the membrane 150 after penetration and advancement of the syringe assembly 100 into the subject S. As shown in FIG. 11C, the plunger protrusion 129 may be withdrawn relative to the barrel 114 after the tip 126 and protrusion 129 engage the membrane 150 so that the protrusion is removed from the tip and the notch 148 of the tip stabilizes the engagement of the tip with the membrane to allow fluid to be exchanged with subject S defined by the membrane and the chamber 116. In various embodiments, the protrusion 129 is sized to have a length extending from the plunger head 120 to the end of the protrusion so that the protrusion extends beyond the tip 126 when the plunger 118 is inserted into to chamber 116 and the plunger head is near, or in contact with, the inner surface of the distal end 117 of the barrel 114. The tip 126 and/or protrusion 129 could be otherwise shaped, arranged, and/or configured without departing from the disclosure.

Those skilled in the art will recognize or be able to ascertain using no more than routine experimentation, many equivalents to the specific embodiments described herein. Such equivalents are intended to be encompassed by the following claims.

The foregoing description of the disclosure illustrates and describes various embodiments. As various changes could be made in the above construction without departing from the scope of the disclosure, it is intended that all matter contained in the above description or shown in the accompanying drawings shall be interpreted as illustrative and not in a limiting sense. Furthermore, the scope of the present disclosure covers various modifications, combinations, alterations, etc., of the above-described embodiments. Additionally, the disclosure shows and describes only selected embodiments, but various other combinations, modifications, and environments are within the scope of the disclosure as expressed herein, commensurate with the above teachings, and/or within the skill or knowledge of the relevant art. Furthermore, certain features and characteristics of each embodiment may be selectively interchanged and applied to other illustrated and non-illustrated embodiments of the disclosure.

What is claimed is:

1. A syringe assembly comprising:

a barrel defining a chamber, the barrel having an open proximal end, a distal end opposite the open proximal end, and a tip extending from the distal end of the barrel, the tip defining a passage that is in fluid communication with the chamber, the tip configured to engage a membrane of a subject; and a plunger having a protrusion that is configured to penetrate the membrane of the subject, the plunger slidably received within the chamber, the plunger slidable from a first position in which the protrusion extends through the passage and beyond the tip such that the protrusion and the tip are insertable into the membrane of the subject towards a second position in which the protrusion is withdrawn from the passage and draws a subject fluid into the chamber through the passage of the tip when the tip is engaged the membrane of the subject.

2. The syringe assembly of claim 1, wherein the plunger has a head and the protrusion extends from the head.

3. The syringe assembly of claim 1, wherein the protrusion has a beveled end.

4. The syringe assembly of claim 1, wherein the protrusion has a pointed end.

5. The syringe assembly of claim 1, wherein the barrel has an external end surface at the distal end and the tip extends from the external end surface, the barrel comprises a collar extending from the external end surface, the tip is concentric with the collar, the collar is configured for attachment of the barrel to a needle assembly.

6. The syringe assembly of claim 5, wherein the collar is generally a hollow cylindrical shape that is configured for connection to a Luer lock connector.

7. The syringe assembly of claim 1, wherein the tip has a tapered external surface that is configured for connection to a Luer slip connector.

8. The syringe assembly of claim 1, wherein the tip has a body, the body has at least one indentation in an external surface of the body for engaging the membrane of the subject.

9. The syringe assembly of claim 8, wherein the at least one indentation is a notch in a portion of the external surface of the body, the notch has edges in the external surface of the body and is shaped to extend less than circumferentially around the external surface.

10. The syringe assembly of claim 8, wherein the at least one indentation is a notch in a portion of the external surface of the body, the notch has edges in the external surface of the body and is shaped to extend circumferentially around the external surface of the body.

11. The syringe assembly of claim 10, wherein the external surface of the body is frustoconical shaped.

12. The syringe assembly of claim 3, wherein the protrusion has a vent passage adjacent the beveled end facilitating flow of fluid into the chamber.

* * * * *